(12) United States Patent
Lunati et al.

(10) Patent No.: US 8,148,692 B2
(45) Date of Patent: Apr. 3, 2012

(54) METHOD FOR ENSURING THE SAFETY OF THE COMPONENTS OF THE DRIVE TRAIN OF A VEHICLE FOLLOWING THE DETERIORATION OF THE FUEL

(75) Inventors: Alain Lunati, La Fare les Olivers (FR); Johan Fournel, Robion (FR)

(73) Assignee: SP3H, Aix en Provence (FR)

( * ) Notice: Subject to any disclaimer, the term of this patent is extended or adjusted under 35 U.S.C. 154(b) by 90 days.

(21) Appl. No.: 12/438,287

(22) PCT Filed: Aug. 2, 2007

(86) PCT No.: PCT/FR2007/001339
§ 371 (c)(1),
(2), (4) Date: Sep. 3, 2009

(87) PCT Pub. No.: WO2008/023104
PCT Pub. Date: Feb. 28, 2008

(65) Prior Publication Data
US 2010/0007874 A1    Jan. 14, 2010

(30) Foreign Application Priority Data
Aug. 21, 2006  (FR) .................................... 06 07420

(51) Int. Cl.
*G01J 5/02*  (2006.01)
(52) U.S. Cl. ...................................................... 250/343
(58) Field of Classification Search .................. 250/343, 250/339.12, 373
See application file for complete search history.

(56) References Cited

U.S. PATENT DOCUMENTS

| 4,770,129 | A |   | 9/1988  | Miyata et al. |
| 5,304,807 | A | * | 4/1994  | Lin ................................ 250/373 |
| 5,349,188 | A | * | 9/1994  | Maggard ................... 250/339.12 |
| 6,121,628 | A | * | 9/2000  | Rising ............................. 250/573 |
| 2002/0144456 | A1 |   | 10/2002 | Degen et al. |
| 2005/0172700 | A1 | * | 8/2005  | Sugiura ......................... 73/61.48 |

FOREIGN PATENT DOCUMENTS

| DE | 34 35 706 A1 | 4/1996 |
| DE | 102 51 837 A1 | 5/2004 |
| DE | 103 49 741 A1 | 6/2005 |
| DE | 10 2005 001 716 A1 | 8/2005 |
| FR | 2 628 836 A1 | 9/1989 |

* cited by examiner

*Primary Examiner* — David Porta
*Assistant Examiner* — Marcus Taningco
(74) *Attorney, Agent, or Firm* — Arent Fox LLP

(57) ABSTRACT

The invention relates to a method of ensuring the safety of the components of the drive train of a vehicle equipped with a heat engine, before or during its startup phase following a deterioration of the quality of the fuel contained in the tank (2) and the fuel feed system of the engine, said method comprising a step of diagnosing the type and extent of the deterioration of the quality of the fuel, said step being based on the measurement of the interactions between an electronmagnetic radiation and the constituent molecules of the fuel, said measurement being performed by a system of analysis, and a step of activating a system (13) to ensure the safety of the components of the drive train as a function of the results of the analysis step.

27 Claims, 3 Drawing Sheets

METHOD FOR ENSURING THE SAFETY OF THE COMPONENTS OF THE DRIVE TRAIN OF A VEHICLE FOLLOWING THE DETERIORATION OF THE FUEL

CROSS-REFERENCE TO RELATED APPLICATION

This application is a National Stage entry on International Application No. PCT/FR2007/001339, filed Aug. 2, 2007, which claims priority to French Patent Application No. 0607420, filed on Aug. 21, 2006, the disclosure of the prior application being incorporated in its entirety by reference.

The invention relates to a preventive method for ensuring the safety of the components of the engine transmission unit of a vehicle equipped with a heat engine before or during its start-up phase following a modification (deterioration, pollution) of the quality of the fuel contained in the tank and the fuel feed system of the engine.

In spite of regulatory or internal provisions made by fuel distributors and vehicle manufacturers such as refiners and distributors' quality audit procedures, the display of the quality of fuel in gas stations, more particularly the diameter of the fuel pump dispensing nozzle and the diameter of the tank filling system, numerous users pour intentionally or not, a non adapted fuel into the tanks of their vehicles. An increasing number of vehicles is used with products which are not certified by the manufacturers and the customs services such as used cooking oil, non esterified vegetal oil, domestic fuel oil which cause important deteriorations in the engine transmission unit, the fuel feed system and the post treatment system thereof. The deteriorations (chocking of injectors, of the engine, of the tank, clogging of the filters, seizing of the pumps, deactivating of the catalysts) can be serious and have a significant impact on the injection and combustion phases of the engine and increase the regulatory or not polluting emissions and can lead to the breaking of the engine. Similarly, some fuels such as water/gas oil or gasoline/alcohol or gas oil/biofuels emulsions can be instable and the quality thereof may deteriorate over time (storage stability, demixing phenomenon between the gasoline and the ethanol or the gas oil and the diester above 5%). Such various sources of deterioration of the quality of the fuel potentially lead to an increase in the pollution of the vehicle, damages to the vehicle or at least significant correcting operations.

The invention aims at meeting the need for a preventive safety of the components of the engine transmission unit of a vehicle equipped with a heat engine, before or during its start up phase following a deterioration of the fuel contained in the tank and the fuel feed system of the engine. The quality and the level of the deteriorations are measured by a system of the microanalyser type, based on the measurement of the interactions between an electromagnetic radiation and the constituent molecules of the fuel, such as for example Carbon, Hydrogen, Oxygen, constituting the fuel. This system is connected to an active or passive system aiming at informing the user visually or with a sound and/or at automatically providing safety to the components of the engine transmission unit.

Innovation makes it possible to solve a known and recurrent problem whose level is increased since it makes it possible to inform the user and/or to preventively stop the start up process of the vehicle in order to confine to the feed system of the vehicle, and thereto only, the impact of the deterioration of the quality of the fuel. A simple change of the oil and rinsing of the tank will be sufficient to restore the operational condition of the vehicle.

For this purpose, the invention relates to a method for ensuring the safety of the components of the drive system of a vehicle equipped with a heat engine, before or during the start up phase following a deterioration of the quality of the fuel contained in the tank and the fuel feed system of the engine, said method being characterised in that it includes a step of diagnosing the type and extent of the deterioration of the quality of the fuel, said step being based on the measurement of the interactions between an electromagnetic radiation and the constituent molecules of the fuel, said measurement being performed by a system of analysis, and the step of activating a system to ensure the safety of the components of the engine transmission unit as a function of the results of the analysis step.

The system of analysis is composed of at least one microanalyser positioned in the fuel circuit including the feed system, the tank, the pumps, the fuel filters, the engine feed circuit and the return circuit to the tank.

The following examples illustrate some of the actions aiming at ensuring the safety of the components of the engine transmission unit, such actions being implemented during the step of activating the system ensuring the safety of the components of the engine transmission unit:

Warning of the user with a sound or visual alarm,
Automatic activating of a system preventing the start of the vehicle,
Automatic activating of the bleed system of the fuel filter or filters,
Automatic activating of the system enabling the bypass of the exhaust post-treatment filters.

The following examples illustrate some possible sources of deterioration or possible pollution of the fuel:

Gasoline poured into the tank of a Diesel-powered vehicle,
Gas oil poured into the tank of a petrol-engined vehicle,
Domestic fuel oil poured into the tank of a petrol-engined or diesel-powered vehicle,
Other products poured into the tank of a petrol-engined or diesel-powered vehicle more particularly:
Products having a high sulfur content,
Products having a high free water molecules content,
Deteriorated water/gas oil emulsion,
Used or not cooking oil,
Non esterified vegetable oil (salad oil),
Demixing (separation) of gasoline/ethanol,
Demixing of gas oil/EMHV.

According to a particular embodiment, the measurement of the interactions between an electromagnetic radiation and the constituent molecules of the fuel by the system of analysis includes a step of spectroscopic analysis of the hydrocarbons composing the fuel. The spectroscopic analysis consists of a near infrared analysis of the fuel.

As a matter of fact, the near infrared analysis is particularly well suited to the diagnosing of the deterioration of the quality of the fuels in that the near infrared analysis is a very sensitive method and in that the near infrared spectrum can be considered as the "DNA" of the product. In addition, the near infrared analysis is particularly repeatable.

It is possible to mention the reference literature for the near infrared as the document by L. G. WEYER, published in 1985 or the "Handbook of near infrared analysis" published in 1992 or more specific publications such as the spectroscopic applications in petroleum chemistry and refining as mentioned in the articles by Jérôme WORKMAN Jr. in 1996 or M. VALLEUR in 1999.

Other objects and advantages of the invention will appear while reading the following description and referring to the appended drawings.

Figure 1:
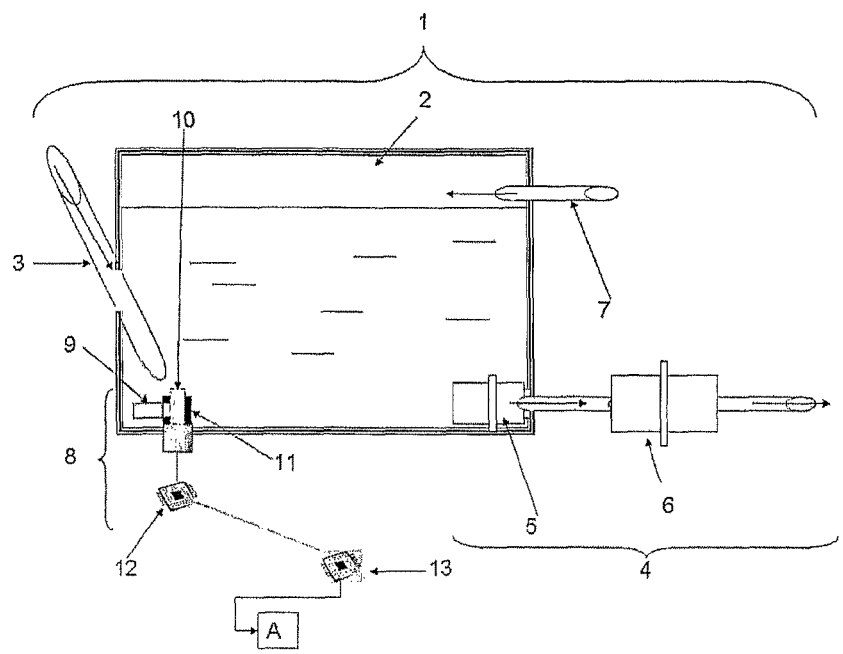
FIG. 1 is a diagrammatic representation of a fuel feed circuit of an engine wherein the method according to the invention is implemented with a first embodiment of the microanalyser of the system of analysis.

While referring to FIG. 1, it describes a method for ensuring the safety of the components of the engine transmission unit of a vehicle equipped with a heat engine before or during the start up phase of the engine using a system of analysis including a microanalyser 8 for diagnosing the deterioration of the quality of the fuel contained in the tank and the fuel feed system of the engine.

The engine is fed with fuel through the fuel circuit 1 including a tank 2, a fuel filling system 3 and a fuel feed circuit 4. The circuit includes for example one or several fuel pumps 5, one or several fuel filters 6 and the return circuit to the tank 7. The method according to the invention is adapted for any type of fuels (gas, liquefied gas, gasoline, kerosene, gas oil, water/gas oil emulsion, fuels, biofuels) meeting the standards on fuels and biofuels with additives or not, the major constituent of which are Carbon, Hydrogen and Oxygen.

The diagnosis of the deterioration of the quality of the fuel contained in the tank and the fuel feed system of the engine consists of a near infrared analysis of the fuel. It could also consist of an infrared analysis or a gas or liquid phase chromatographic analysis or an RMN analysis or an ultraviolet analysis, or of several research analyses simultaneously made according to the same principle.

According to one embodiment shown in FIG. 1, a spectroscopic microanalyser 8 is positioned in the fuel circuit 1 and is connected to an electronic or digital system for ensuring the safety 13 of the components of the engine transmission unit in an active or passive way (A). The system ensuring the safety 13 is an active or passive system informing the engine calculator.

In the case of a near infrared analysis, the microanalyser 8 is composed of a light source 9, a light separation system, a fuel sampling cell 10, a photosensitive detection system 11 and a dedicated calculator 12. The dedicated calculator 12 makes it possible to pilot the measuring sequences, to adjust and control the correct operation of the microanalyser 8. The calculator 12 contains the models making it possible to carry out all the calculations associated with the processing of the near infrared spectrum. The calculator 12 is connected to the electronic or digital system for ensuring the safety 13 of the components of the engine transmission unit in an active or passive way.

In the case of a near infrared analysis, the microanalyser 8 may include only one source and only one detector or several light sources and one detector or one source and several detectors or several light sources and several detectors. It can use, in the case of the non dispersive near infrared, interferential filters or crystal filters or a Fourier transform system. The microanalyser 8 can be of the multiplex or the sequential access types.

Figure 2:
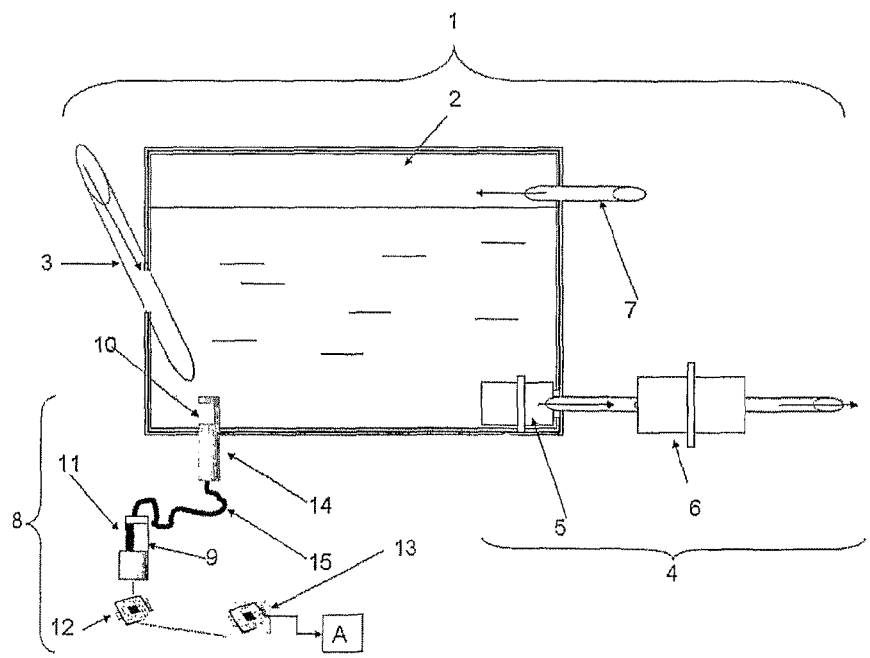
FIG. 2 is a schematic representation similar to FIG. 1 with a second embodiment of the microanalyser of the system of analysis.

According to another embodiment shown in FIG. 2, the use of optical fibers 15 and an adapted dipping probe 14 is possible for moving the system sampling the other components of the microanalyser 8.

The microanalyser 8 can be a plate strap near infrared spectrometer composed of a plurality of photodiodes, each emitting a light intensity at a given wavelength. The detector 11 is a high sensitive silicon-based or complex alloy (InGaAs, InAs, InSb, PbS, PbSe)-based semi-conductor. The detector 11 can be cooled or not.

Figure 3:
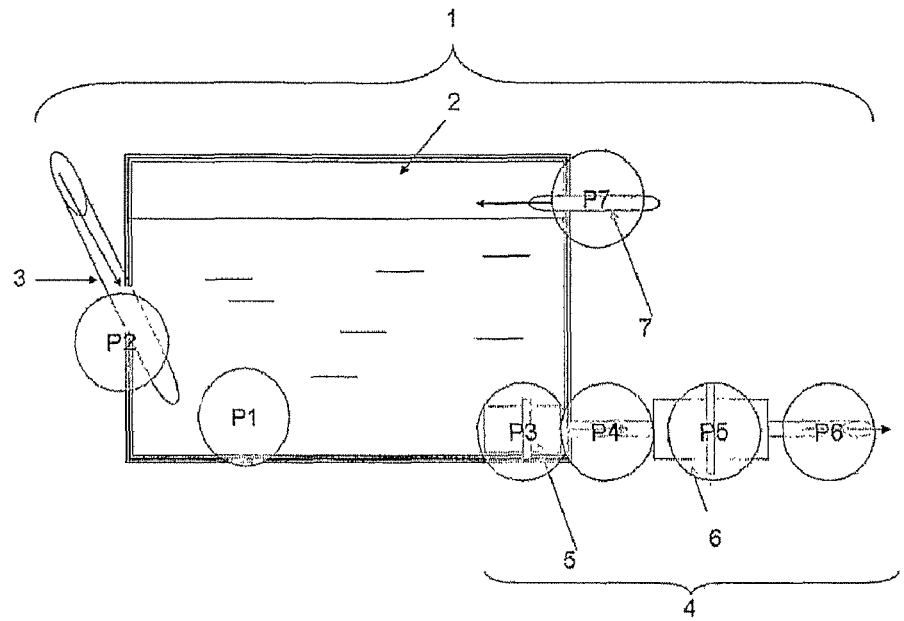
FIG. 3 is a schematic representation of the fuel feed circuit of an engine, wherein the various possibilities for positioning the system of analysis of the method according to the invention are shown.

FIG. 3 shows that the microanalyser 8 can be positioned in the tank (Position P1), at the level of the tank filling system (Position P2), in the fuel feed circuit of the engine 4. In the later case, the microanalyser 8 can be positioned in the pump (Position P3), between the pump 5 and the filter 6 (Position P4) in the filter 6 (Position P5) or after the filter 6 (Position P6). The microanalyser can also be positioned in the fuel return circuit 7 (Position P7).

The microanalyser is so arranged as to make measurements in the spectral regions between 780 and 2,500 nanometers (12,820 $cm^{-1}$ to 4,000 $cm^{-1}$). Successive measuring ranges can for example be provided between 780 nanometers and 1,100 nanometers (12,820 $cm^{-1}$ to 9,090 $cm^{-1}$), 1,100 nanometers and 2,000 nanometers (9,090 $cm^{-1}$ to 5,000 $cm^{-1}$) and 2,000 nanometers and 2,500 nanometers (5,000 $cm^{-1}$ to 4,000 $cm^{-1}$). For this purpose, the sampling system is so arranged as to show an optical path, i.e. a thickness of the measuring cell through which the measurement is made, between 0.5 millimeters and 100 millimeters, i.e. optical paths corresponding to the wavelength ranges from 50 millimeters to 100 millimeters in the first case, from 10 millimeters to 20 millimeters in the second case and from 0.5 millimeters to 5 millimeters in the last case.

The microanalyser 8 is so arranged as to make the near infrared spectrum of the fuel circulating in the fuel feed circuit 1 of the engine in reflectance, in transmittance, in absorbance or in diffusion.

The microanalyser 8 has a spectral resolution (accuracy) which can be adjusted from 1 $cm^{-1}$ to 20 $cm^{-1}$, preferably 4 $cm^{-1}$.

The optical and sampling system of the microanalyser 8 can also be self-cleaning which avoids having to dismount it prior to cleaning it.

Figure 4:
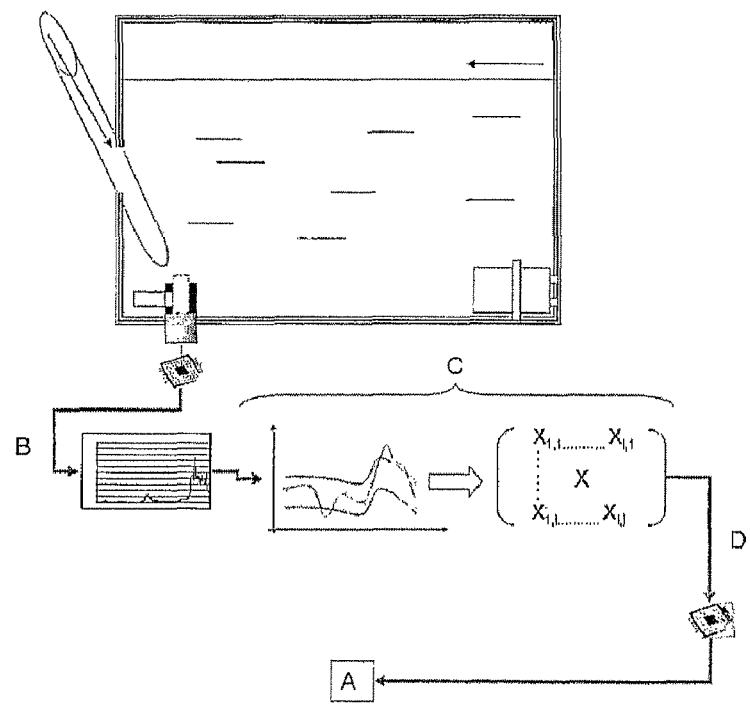
FIG. 4 is a diagram showing the main steps of the method.

FIG. 4 shows the various steps of the method:
B: Collection of the near infrared spectrum;
C: Mathematical method making it possible to show a deterioration of the quality of the fuel, the type and the level thereof;
D: Transfer of the addressing table of the calculator (12) of the microanalyser (8) to the system ensuring an active or a passive safety 13 of the components of the engine transmission unit.
A: Ensuring an active or a passive safety of the components of the engine transmission unit.

Figure 5:
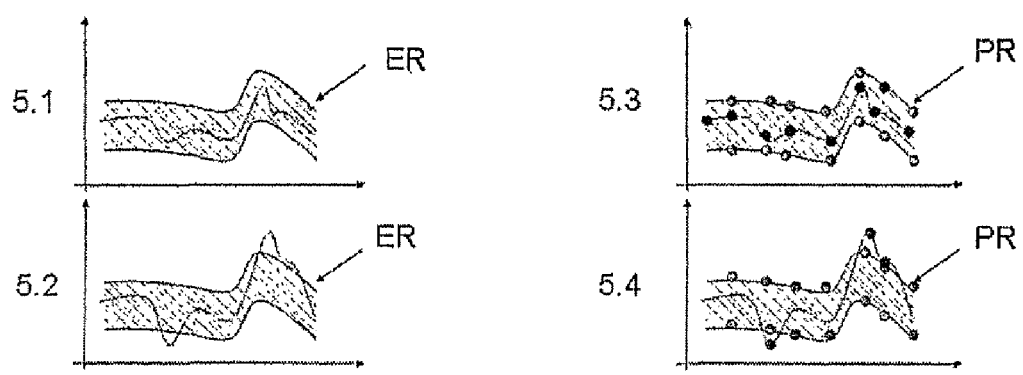
FIG. 5 shows two methods for evidencing the deterioration of the fuel.

FIG. 5 illustrates the mathematical method for determining the deterioration of the quality of the fuel. The measurements of the near infrared spectrum of the fuel are made for example in absorbance in the considered wavelength areas. The values of the absorbance measured for each selected wavelength are compared to one or to several spectrum envelopes (ER) (5.1 and 5.2) or reference points (PR) (5.3 and r.4), so as to determine the existence of a deterioration of the quality of the fuel and more precisely the type and the level (scale) of such deterioration. In examples 5.1 and 5.3, the values of the absorbance of the fuel measured for each selected wavelength are included in the spectrum envelopes (ER) or reference points (PR) which makes it possible to deduce an absence of remarkable deterioration of the fuel. In examples 5.2 and 5.4, the values of the absorbance of the fuel measured for each selected wavelength are not included in the spectrum envelopes (ER) or reference points (PR), which makes it possible to deduce the existence of a remarkable deterioration of the fuel; the type of the deterioration can be determined when studying the wavelength, the absorbance of which are outside the spectrum envelopes or reference points; the deviations between the absorption measured for each selected wavelength and the spectrum envelopes or reference points, make it possible to determine the level (scale) of such deterioration. The system further includes self-diagnosing means making it possible to automatically validate the result or results and to automatically evidence the malfunction of the system. The self-diagnosing means make it possible to ensure the correct operation of the system or if need be to inform the user, the EOBD and the engine control The result or the results is or are sent to the system or systems ensuring the active or passive security 13 of the components of the engine transmission unit.

An exemplary table (FIG. 3[X]) addressed by the calculator 12 of the microanalyser 8 to the system ensuring the active or passive safety 13 of the components of the engine transmission unit is shown in the table hereinunder. The table is that obtained for a deterioration of the quality of the fuel due to the introduction of water.

| Deterioration | Type of deterioration | Level of deterioration | Self-diagnosis status |
|---|---|---|---|
| Yes | Water | 3 | OK |

In the case when a deterioration of the quality of the fuel is detected, the digital or electronic system 13 can automatically ensure the safety of the components of the engine transmission unit or inform the user with a visual or sound alarm, with the aim of preventing a deterioration of the engine transmission unit.

A step of storing the deteriorations of the quality of the fuel, the type and the level thereof, is used so as to make a precise history of such deteriorations.

The active system ensuring the safety 13 can act directly or indirectly on the fuel circuit parameters, the fuel injection parameters, the combustion parameters, the post-treatment parameters and/or the vehicle start up parameters.

The invention claimed is:

1. A method for ensuring safety of components of a drive train of a vehicle equipped with a heat engine before or during a start up phase following a deterioration of quality of fuel contained in a tank and the fuel feed system of the engine, said method comprising:
    a step of diagnosing a type and extent of the deterioration of the quality of the fuel, said step of diagnosing comprising a step of determination of a molecular structure of the fuel, said determination being performed by a system of analysis, including at least one spectroscopic microanalyser; and
    a step of activating a system to ensure the safety of the components of the drive train as a function of the results of the analysis step,
    wherein the step of determination of said molecular structure of the fuel is based on an infrared spectroscopic analysis using said spectroscopic microanalyser.

2. A method according to claim 1, wherein the system for ensuring the safety is a user sound or visual alarm system.

3. A method according to claim 1, wherein the system for ensuring the safety is an active or passive system informing an engine calculator.

4. A method according to claim 3, wherein the active system for ensuring safety acts directly or indirectly on fuel circuit parameters, fuel injection parameters, combustion parameters, post-treatment parameters and/or start-up parameters of the vehicle.

5. A method according to claim 1, wherein the step of activating a system for ensuring safety includes the automatic activating of a system preventing the vehicle to start up.

6. A method according to claim 1, wherein the step of activating a system for ensuring safety includes the automatic activating of a fuel filter or filters bleed system.

7. A method according to claim 1, wherein the step of automatic activating of a system for ensuring safety includes the activating of a system allowing the bypass of exhaust post-treatment filters.

8. A method according to any one of claims 1 to 7, wherein the system for providing safety includes self-diagnosis means for ensuring the correct operation of the system or if need be for informing a user, an EOBD and the engine control.

9. A method according to claim 1, wherein the step of diagnosing the deterioration of the quality of the fuel includes a step of addressing at least one table including values of criteria representing the quality, the type and the level of deterioration of the fuel, intended for the system ensuring the safety.

10. A method according to claim 1, wherein the measurement of interactions between electromagnetic radiations and the constituent molecules of the fuel consists of a near, infrared spectroscopic analysis.

11. A method according to claim 1, wherein said microanalyser is positioned in a fuel circuit including a filling system, the tank, pumps, fuel filters, the engine fuel feed system, and a return circuit to the tank.

12. A method according to claim 1, wherein the spectroscopic microanalyser (8) is a near infrared microanalyser.

13. A method according to claim 12, wherein the near infrared microanalyser is arranged to perform measurements in the spectral regions between 780 nm and 2500 nm.

14. A method according to claim 12, wherein the microanalyser is arranged to provide an optical path wherein a thickness of a measuring cell is between 0.5 mm and 100 mm and to perform measurements in the spectral regions between 780 nm and 2500 nm.

15. A method according to claim 12, wherein the microanalyser is arranged to provide a spectral resolution wherein a measuring accuracy is between $1\ cm^{-1}$ and $20\ cm^{-1}$ and to perform measurements in the spectral regions between 780 nm and 2500 nm.

16. A method according to claim 11, wherein a microanalyser made from a light source, a sampling cell, an optical treatment system (selection, attenuation, amplification) of the light, a detector and a calculator.

17. A method according to claim 11, wherein a microanalyser made from a dipping probe and optical fibers is used.

18. A method according to claim 11, wherein a microanalyser made with an instrument including a plurality of band infrared emitting diodes is used.

19. A method according to claim 11, wherein a microanalyser made with an instrument including a detector composed of high sensitivity photosensitive diodes is used.

20. A method according to claim 11, wherein a microanalyser made with an instrument including a polychromatic infrared light source is used.

21. A method according to claim 11, wherein a microanalyser made with an instrument including a wavelength selection system is used.

22. A method according to claim 11, wherein a microanalyser made from at least one Fourier transform instrument is used.

23. A method according to claim 11, wherein the microanalyser is self-cleaning.

24. A method according to claim 11, wherein the microanalyser is positioned in the fuel tank in the tank filling system, between the fuel pump and the fuel filter, in the fuel filter, downstream of the fuel filter or in the return circuit.

25. A method according to any claim 11, wherein the measures of the near infrared spectra of the fuel are made in absorbance, in reflectance, in transmittance or in diffusion in the considered wavelength areas.

26. A method according to claim 25, wherein the values of the absorbance, reflectance, transmittance or diffusion measured for each selected wavelength are compared to one or several spectrum envelopes or reference points so as to determine the existence of a deterioration of the fuel quality and more particularly the type and the level (scale) of such deterioration.

27. A method according to claim 1, further comprising storing information on the type and the level of the deterioration of the quality of the fuel so as to make a history.

* * * * *